United States Patent [19]

Hallenbach et al.

[11] Patent Number: 4,760,063
[45] Date of Patent: Jul. 26, 1988

[54] THIENOOXAZINONES, PROCESSES FOR THEIR PREPARATION, AND THEIR USE AS GROWTH PROMOTERS

[75] Inventors: Werner Hallenbach, Langenfeld; Hans Lindel, Leverkusen; Friedrich Berschauer, Wuppertal; Martin Scheer, Wuppertal; Anno de Jong, Wuppertal, all of Fed. Rep. of Germany

[73] Assignee: Bayer Aktiengesellschaft, Leverkusen, Fed. Rep. of Germany

[21] Appl. No.: 929,921

[22] Filed: Nov. 12, 1986

[30] Foreign Application Priority Data

Nov. 14, 1985 [DE] Fed. Rep. of Germany ....... 3540377

[51] Int. Cl.$^4$ ..................... A61K 31/38; C07D 265/04
[52] U.S. Cl. ................................. 514/230.5; 544/91; 544/92; 544/95
[58] Field of Search ....................... 544/91, 95, 92, 89; 514/231, 443, 444; 71/90; 549/288

[56] References Cited

U.S. PATENT DOCUMENTS 4,036,979  7/1977  Asato ............... 514/231 X
4,234,581  11/1980  Temple ............. 544/91 X

FOREIGN PATENT DOCUMENTS 2315303  10/1974  Fed. Rep. of Germany .

OTHER PUBLICATIONS

Shvedov et al., Chemical Abstracts, vol. 66 (1967) 37711w.

*Primary Examiner*—Glennon H. Hollrah
*Assistant Examiner*—S. Treanor
*Attorney, Agent, or Firm*—Sprung, Horn Kramer & Woods

[57] ABSTRACT

Novel thienooxazines of the formula

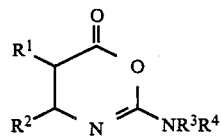

in which
$R^1$ and $R^2$, together with the adjacent C atoms, represent an optionally substituted thiophene ring,
$R^3$ represents hydrogen, optionally substituted alkyl, cycloalkyl, alkenyl or aryl, and
$R^4$ represents optionally substituted alkyl, cycloalkyl, alkenyl or aryl, or
$R^3$ and $R^4$, together with the adjacent nitrogen atom, form a saturated heterocyclic structure which may optionally contain further hetero atoms, promote the yield of animals, e.g. rate of growth, ratio of meat to fat, etc. They are made from new intermediates of the formulas

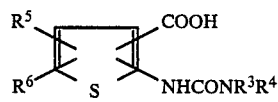

and

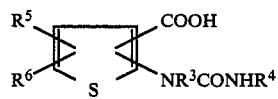

in which
$R^5$ and $R^6$ may be hydrogen or various organic radicals, or together form a ring.

6 Claims, No Drawings

THIENOOXAZINONES, PROCESSES FOR THEIR PREPARATION, AND THEIR USE AS GROWTH PROMOTERS

The present invention relates to thienooxazinones, processes for their preparation, and their use as yield-promoting agents for animals.

Benzoxazinones are known (see DE-OS (German Published Specification) No. 2,315,303). Thienooxazinones represent a structurally completely novel class of compounds and cannot be compared with benzoxazinones either in terms of their structure or in terms of their properties.

The following have now been found:
1. New thienooxazinones of the formula I

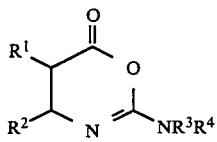

in which
$R^1$ and $R^2$, together with the adjacent C atoms, represent an optionally substituted thiophene ring,
$R^3$ represents hydrogen, optionally substituted alkyl, cycloalkyl, alkenyl or aryl, and
$R^4$ represents optionally substituted alkyl, cycloalkyl, alkenyl or aryl, or
$R^3$ and $R^4$, together with the adjacent nitrogen atom, represent an optionally substituted saturated heterocyclic structure which may optionally contain further hetero atoms.

The thienooxazinones of the formula I may be present in the form of their isomers of the formula Ia and as mixtures of the two isomeric forms.

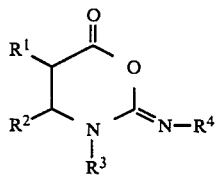

2. Process for the preparation of the new thienooxazinones of the general formula

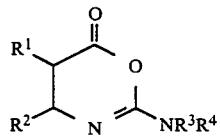

in which
$R^1$ and $R^2$, together with the adjacent C atoms, represent an optionally substituted thiophene ring,
$R^3$ represents hydrogen, optionally substituted alkyl, cycloalkyl, alkenyl or aryl, and
$R^4$ represents optionally substituted alkyl, cycloalkyl, alkenyl or aryl, or
$R^3$ and $R^4$, together with the adjacent nitrogen atom, represent an optionally substituted heterocyclic structure which can optionally contain further hetero atoms, characterized in that
(a) thienylureas of the formula II

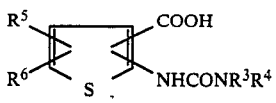

or IIa

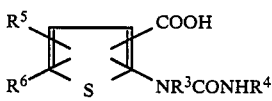

in which
$R^5$ and $R^6$ represent identical or different radicals from the group comprising hydrogen, halogen, nitro, CN, alkyl, alkoxy, alkylthio, aryl, alkylcarbonyl, alkoxycarbonyl, arylcarbonyl and aryloxycarbonyl, which may optionally be substituted, or
$R^5$ and $R^6$, together with the adjacent C atoms, may furthermore represent an optionally substituted saturated or unsaturated carbocyclic ring, and
$R^3$ and $R^4$ have the meaning given above, and the radicals —COOH, —NHCONR$^3$R$^4$ or —NR$^3$CONHR$^4$ are adjacent to one another,
are reacted with condensing agents, or
(b) aminothiophenes of the formula III

in which
$R^5$ and $R^6$ have the meaning given above and the radicals COOH and NH$_2$ are adjacent to one another,
are reacted with at least 1 mol (per mol of aminothiophene of the formula III) of the compounds of the formula IV

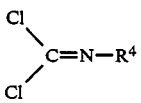

in which
$R^4$ has the meaning given above,
or
(c) by reacting compounds of the formula V

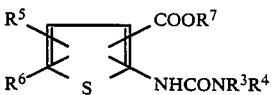

or their isomers of the formula Va

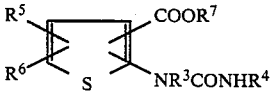

in which
$R^3$, $R^4$, $R^5$ and $R^6$ have the meaning given above, and $R^7$ represents tertiary alkyl radicals or benzyl, with acidic condensing agents mixed with dehydrating agents.

3. Compounds of the formulae II and IIa

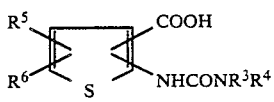   (II)

or IIa

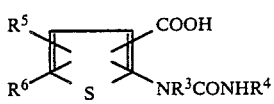   (IIa)

in which $R^3$ represents hydrogen, optionally substituted alkyl, cycloalkyl, alkenyl or aryl, $R^4$ represents optionally substituted alkyl, cycloalkyl, alkenyl or aryl, and $R^5$ and $R^6$ represent identical or different radicals from the group comprising hydrogen, halogen, nitro, CN, alkyl, alkoxy, alkylthio, aryl, alkylcarbonyl, alkoxycarbonyl, arylcarbonyl and aryloxycarbonyl, which may optionally be substituted, or $R^5$ and $R^6$, together with the adjacent C atoms, may furthermore represent an optionally substituted saturated or unsaturated carbocyclic ring, with the exception of the unsubstituted phenyl ring, are new.

4. Process for the preparation of the compounds of the formulae II and IIa according to section 3 (above), characterized in that (a) compounds of the formulae V and Va in which $R^3$, $R^4$, $R^5$, $R^6$ and $R^7$ have the meanings given under section 2c (above), are reacted with strong acids or (b) compounds of the formula VI

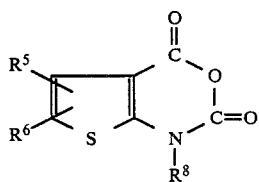   (VI)

in which $R^5$ and $R^6$ have the meaning given under section 3, and $R^8$ represents hydrogen or optionally substituted alkyl, cycloalkyl, alkenyl or aryl, are reacted with amines of the formula VII

   (VII)

in which $R^3$ and $R^4$ have the meaning given under section 3, with the precondition that, if $R^8$ represents optionally substituted alkyl, cycloalkyl, alkenyl or aryl, the radical $R^3$ represents hydrogen.

The fact that thienooxazinones of the formula I possess yield-promoting properties in animals was completely surprising. This use of this class of compounds was not indicated at all in the prior art.

Preferred thienooxazinones of the formula I are those in which $R^1$ and $R^2$, together with the adjacent C atoms, represent a thiophene ring which is fused to the oxazinone ring in the 1,2- or 2,3-position. The thiophene ring is substituted by the radicals $R^5$ and $R^6$.

$R^5$ preferably represents hydrogen, halogen, nitro, CN, $C_{1-4}$-alkoxy, $C_{1-4}$-alkylthio, optionally substituted $C_{1-6}$-acyl, or optionally substituted aroyl, in particular benzoyl, or preferably represents $C_{1-6}$-alkyl which is optionally substituted by halogen, $C_{1-4}$-alkoxy, $C_{1-4}$-alkylthio, aryl, in particular phenyl, aryloxy, in particular phenoxy, arylthio, in particular phenylthio, amino, $C_{1-4}$-alkylamino, di-$C_{1-4}$-alkylamino or arylamino, in particular phenylamino, and represents phenyl, the phenyl radicals optionally carrying one or more of the following substituents: halogen, $C_{1-4}$-alkyl, CN, $C_{1-4}$-alkoxy, $C_{1-4}$-alkylthio, phenyl, phenoxy, phenylthio, amino, $C_{1-4}$-alkylamino, di-$C_{1-4}$-alkylamino, $C_{1-4}$-alkoxyalkyl, $C_{1-4}$-halogenoalkyl, $C_{1-4}$-halogenoalkoxy, $C_{1-4}$-halogenoalkylthio, methylenedioxy or ethylenedioxy, which are optionally halogen-substituted, or acyl, $R^6$ represents the radicals listed for $R^5$, or $R^5$ and $R^6$, together with the two adjacent C atoms, represent saturated or unsaturated carbocyclic radicals having 5-8 ring members, which are optionally substituted by OH, $C_{1-4}$-alkyl, halogen, nitro, CN, $C_{1-4}$-alkoxy, $C_{1-4}$-alkylthio, phenyl, phenoxy, phenylthio, amino, $C_{1-4}$-alkylamino, $C_{1-4}$-dialkylamino, $C_{1-4}$-halogenoalkyl, $C_{1-4}$-halogenoalkoxy, $C_{1-4}$-halogenoalkylthio or $C_{1-4}$-alkoxyalkyl, $R^3$ represents hydrogen, and $R^4$ represents $C_{1-4}$-alkyl which is optionally substituted by halogen, $C_{1-4}$-alkoxy, $C_{1-4}$-alkylthio, aryl, in particular phenyl, aryloxy, in particular phenoxy, arylthio, in particular phenylthio, or amino, and furthermore represents phenyl, the phenyl radicals optionally carrying one or more of the following substituents: halogen, $C_{1-4}$-alkyl, CN, $C_{1-4}$-alkoxy, $C_{1-4}$-alkylthio, phenyl, phenoxy, phenylthio, amino, $C_{1-4}$-alkylamino, di-$C_{1-4}$-alkylamino, $C_{1-4}$-halogenoalkoxy, $C_{1-4}$-halogenoalkylthio, methylenedioxy or ethylenedioxy, which are optionally halogen-substituted, or acyl. Particularly preferred compounds of the formula I are those in which $R^1$ and $R^2$ represent a thiophene ring which is fused to the oxazinone ring in the 1,2-position and is substituted by the radicals $R^5$ and $R^6$.

In this formula, $R^5$ preferably represents hydrogen or $C_{1-6}$-alkyl which is optionally substituted by fluorine, chlorine or bromine, or preferably represents phenyl which is optionally substituted by $C_{1-4}$-alkyl, halogen, $C_{1-4}$-halogenoalkyl, in particular trifluoromethyl, or $C_{1-4}$-halogenoalkoxy, in particular trifluoromethoxy, or represents nitro or acyl, in particular acetyl, $R^6$ represents the radicals stated in the case of $R^5$, or $R^5$ and $R^6$, together with the adjacent C atoms, preferably represent a saturated 5- to 8-membered carbocyclic ring which is optionally substituted by $C_{1-4}$-alkyl, and, together with the adjacent C atoms, preferably represent a fused benzene ring which is optionally substituted by halogen, in particular chlorine, nitro or $C_{1-4}$-alkyl, $R^3$ represents hydrogen, and $R^4$ represents $C_{1-6}$-alkyl or cycloalkyl having up to 8 C atoms or represents phenyl which is optionally substituted by halogen, in particular chlorine, or nitro.

In particular, compounds of the formula I may be mentioned in which $R^1$ and $R^2$, together with the adjacent C atoms, represent a thiophene ring which is fused to the oxazinone ring in the 1,2-position and is substituted by $R^5$ and $R^6$.

$R^5$ preferably represents hydrogen, $C_{1-4}$-alkyl, in particular methyl, ethyl or t-butyl, acetyl, phenyl or nitro, $R^6$ preferably represents the radicals listed in the case of $R^5$, or $R^5$ and $R^6$ together preferably represent a cyclopentane, cyclohexane, cycloheptane, cyclooctane, cyclohexanone or benzene ring which is fused to the thiophene ring and optionally can be substituted by $C_{1-4}$-alkyl, in particular methyl, halogen, in particular chlorine, or nitro, $R^3$ preferably represents hydrogen and $R^4$ preferably represents $C_{1-6}$-alkyl, in particular methyl, ethyl, propyl or t-butyl, cycloalkyl having up to 6 C atoms, or phenyl which is optionally substituted by halogen, in particular chlorine.

The following compounds of the formula I may be mentioned individually:

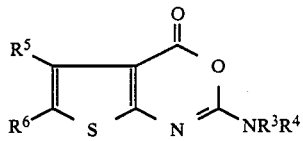

| $R^5$ | $R^6$ | $R^3$ | $R^4$ |
|---|---|---|---|
| H | —CH(CH₃)₂ | H | —CH₃ |
| H | —CH(CH₃)₂ | H | —CH(CH₃)₂ |
| H | —CH(CH₃)₂ | H | cyclohexyl |
| H | —CH(CH₃)₂ | H | phenyl |
| H | —CH(CH₃)₂ | H | sec. butyl |
| H | —CH₂—CH(CH₃)₂ | H | —CH₃ |
| H | —CH₂—CH(CH₃)₂ | H | —CH(CH₃)₂ |
| H | —CH₂—CH(CH₃)₂ | H | cyclohexyl |
| H | —CH₂—CH(CH₃)₂ | H | phenyl |
| H | —CH₂—CH(CH₃)₂ | H | sec.-butyl |
| H | —CH₂—CH(CH₃)₂ | H | tert.-butyl |
| H | —CH(CH₃)₂ | H | tert.-butyl |
| —CH₃ | —Et | H | —CH(CH₃)₂ |
| —CH₃ | —Et | H | phenyl |
| (CH₂)₃ | | H | CH₃ |
| (CH₂)₃ | | H | i-propyl |
| (CH₂)₃ | | H | n-butyl |
| (CH₂)₃ | | H | cyclohexyl |
| (CH₂)₃ | | H | phenyl |
| (CH₂)₃ | | H | 4-chlorophenyl |
| (CH₂)₄ | | H | CH₃ |
| (CH₂)₄ | | H | i-propyl |
| (CH₂)₄ | | CH₃ | n-butyl |
| (CH₂)₄ | | CH₃ | cyclohexyl |
| (CH₂)₄ | | C₂H₅ | CH₃ |
| (CH₂)₄ | | CH₃ | phenyl |
| (CH₂)₄ | | CH₃ | 4-chlorophenyl |
| (CH₂)₄ | | C₂H₅ | i-propyl |
| (CH₂)₄ | | CH₃ | 2-methylphenyl |
| (CH₂)₄ | | CH₃ | 2-methoxyphenyl |
| (CH₂)₄ | | C₂H₅ | n-butyl |
| (CH₂)₅ | | CH₃ | CH₃ |
| (CH₂)₅ | | CH₃ | i-propyl |
| (CH₂)₅ | | C₂H₅ | CH₃ |
| (CH₂)₅ | | CH₃ | n-butyl |
| (CH₂)₅ | | CH₃ | cyclohexyl |
| (CH₂)₅ | | C₂H₅ | i-propyl |
| (CH₂)₅ | | CH₃ | phenyl |
| (CH₂)₅ | | C₂H₅ | n-butyl |

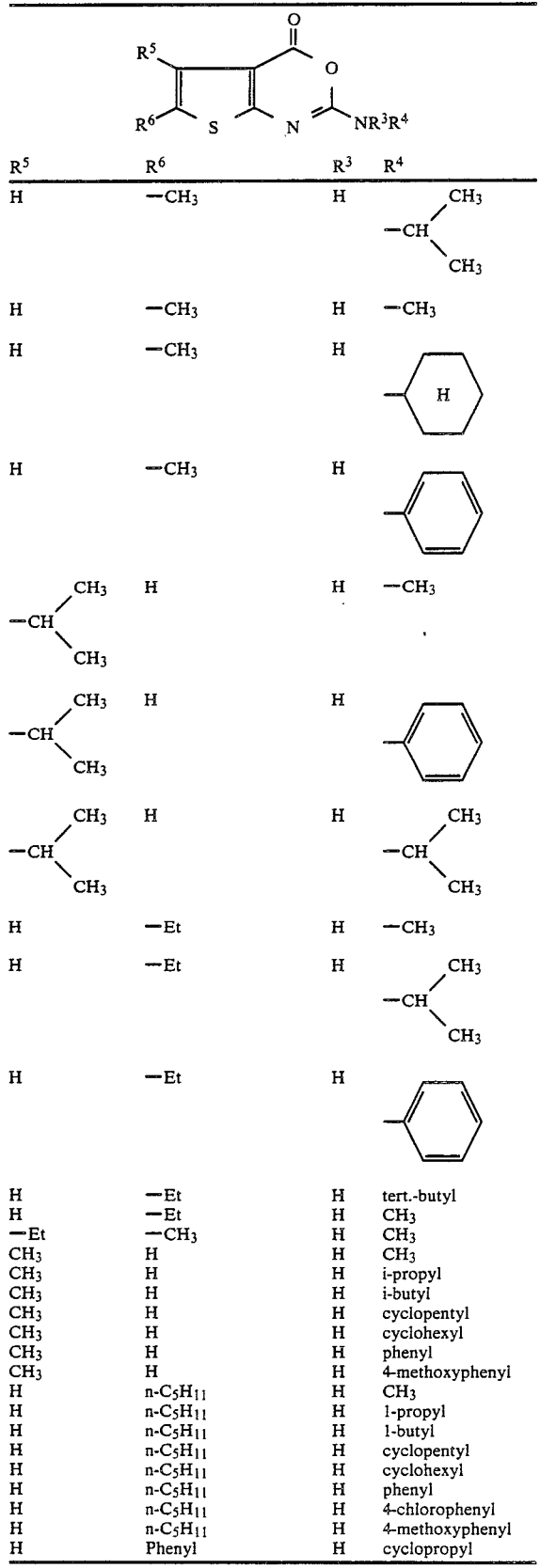

the reaction in process 2a for the preparation of the thienooxazinones can be represented as follows:

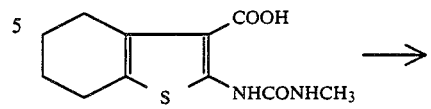

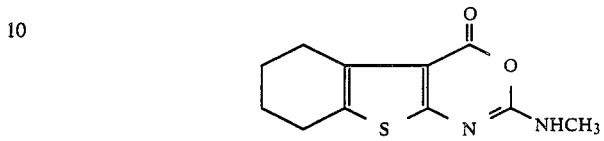

Preferably used starting compounds of the formula II are those in which the radicals $R^3$, $R^4$, $R^5$ and $R^6$ have the preferred meanings mentioned in the case of the compounds of the formula I.

The compounds of the formula II are new. Their preparation is described further below.

The following compounds of the formula II may be mentioned individually:

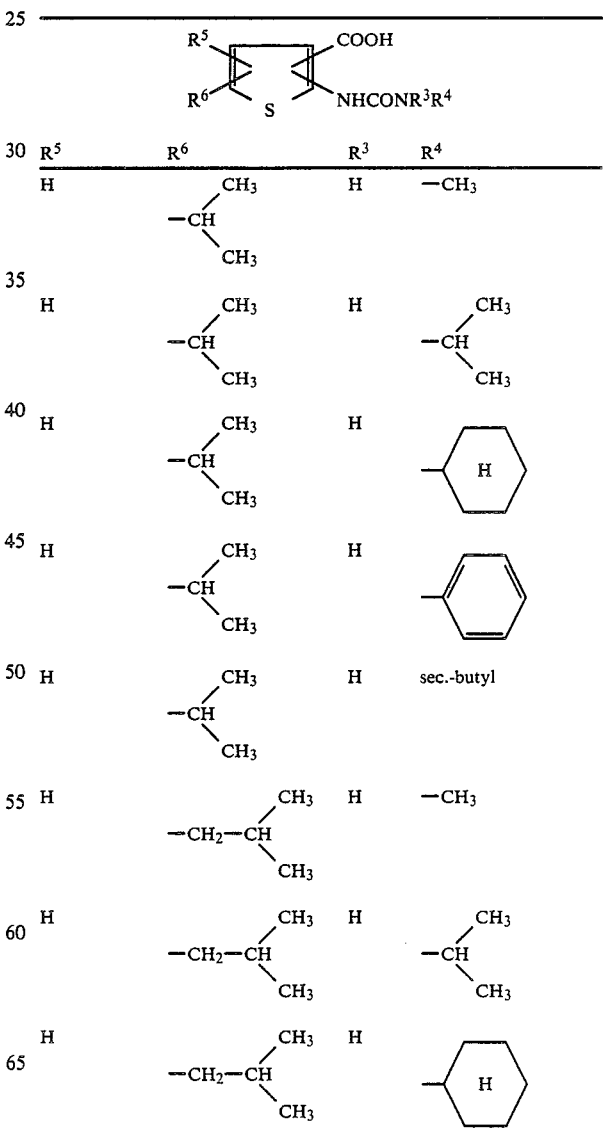

If 2-N'-methylureido-3-carboxy-4,5-tetramethylene-thiophene is used as a starting compound, the course of -continued $$\begin{array}{c} R^5 \\ R^6 \end{array}\!\!\diagup\!\!\!\diagdown\!\!\begin{array}{c} COOH \\ NHCONR^3R^4 \end{array}$$

| $R^5$ | $R^6$ | $R^3$ | $R^4$ |
|---|---|---|---|
| H | —CH$_2$—CH(CH$_3$)$_2$ | H | phenyl |
| H | —CH$_2$—CH(CH$_3$)$_2$ | H | sec.-butyl |
| H | —CH$_2$—CH(CH$_3$)$_2$ | H | tert.-butyl |
| H | —CH(CH$_3$)$_2$ | H | tert.-butyl |
| —CH$_3$ | —Et | H | —CH(CH$_3$)$_2$ |
| —CH$_3$ | —Et | H | phenyl |
| (CH$_2$)$_3$ | | H | CH$_3$ |
| (CH$_2$)$_3$ | | H | i-propyl |
| (CH$_2$)$_3$ | | H | n-butyl |
| (CH$_2$)$_3$ | | H | cyclohexyl |
| (CH$_2$)$_3$ | | H | phenyl |
| (CH$_2$)$_3$ | | H | 4-chlorophenyl |
| (CH$_2$)$_4$ | | H | CH$_3$ |
| (CH$_2$)$_4$ | | H | i-propyl |
| (CH$_2$)$_4$ | | CH$_3$ | n-butyl |
| (CH$_2$)$_4$ | | CH$_3$ | cyclohexyl |
| (CH$_2$)$_4$ | | C$_2$H$_5$ | CH$_3$ |
| (CH$_2$)$_4$ | | CH$_3$ | phenyl |
| (CH$_2$)$_4$ | | CH$_3$ | 4-chlorophenyl |
| (CH$_2$)$_4$ | | C$_2$H$_5$ | i-propyl |
| (CH$_2$)$_4$ | | CH$_3$ | 2-methylphenyl |
| (CH$_2$)$_4$ | | CH$_3$ | 2-methoxyphenyl |
| (CH$_2$)$_4$ | | C$_2$H$_5$ | n-butyl |
| (CH$_2$)$_5$ | | CH$_3$ | CH$_3$ |
| (CH$_2$)$_5$ | | CH$_3$ | i-propyl |
| (CH$_2$)$_5$ | | C$_2$H$_5$ | CH$_3$ |
| (CH$_2$)$_5$ | | CH$_3$ | n-butyl |
| (CH$_2$)$_5$ | | CH$_3$ | cyclohexyl |
| (CH$_2$)$_5$ | | C$_2$H$_5$ | i-propyl |
| (CH$_2$)$_5$ | | CH$_3$ | phenyl |
| (CH$_2$)$_5$ | | C$_2$H$_5$ | n-butyl |
| H | —CH$_3$ | H | —CH(CH$_3$)$_2$ |
| H | —CH$_3$ | H | —CH$_3$ |
| H | —CH$_3$ | H | cyclohexyl |
| H | —CH$_3$ | H | phenyl |
| H | —CH(CH$_3$)$_2$ | H | —CH$_3$ |
| H | —CH(CH$_3$)$_2$ | H | phenyl |
| H | —CH(CH$_3$)$_2$ | H | —CH(CH$_3$)$_2$ |
| H | —Et | H | —CH$_3$ |
| H | —Et | H | —CH(CH$_3$)$_2$ |
| H | —Et | H | phenyl |
| H | —Et | H | tert.-butyl |
| H | —Et | H | —CH$_3$ |
| —Et | —CH$_3$ | H | —CH$_3$ |
| CH$_3$ | H | H | CH$_3$ |
| CH$_3$ | H | H | i-propyl |
| CH$_3$ | H | H | i-butyl |
| CH$_3$ | H | H | cyclopentyl |
| CH$_3$ | H | H | cyclohexyl |
| CH$_3$ | H | H | phenyl |
| CH$_3$ | H | H | 4-methoxyphenyl |
| H | n-C$_5$H$_{11}$ | H | CH$_3$ |
| H | n-C$_5$H$_{11}$ | H | 1-propyl |
| H | n-C$_5$H$_{11}$ | H | 1-butyl |
| H | n-C$_5$H$_{11}$ | H | cyclopentyl |
| H | n-C$_5$H$_{11}$ | H | cyclohexyl |
| H | n-C$_5$H$_{11}$ | H | phenyl |
| H | n-C$_5$H$_{11}$ | H | 4-chlorophenyl |
| H | n-C$_5$H$_{11}$ | H | 4-methoxyphenyl |
| H | Phenyl | H | cyclopropyl |

Suitable condensing agents for the reaction are lower aliphatic carboxylic anhydrides, for example acetic anhydride, propionic anhydride, and butyric anhydride; halogen-substituted aliphatic carboxylic anhydrides, such as trifluoroacetic anhydride; and dicyclohexylcarbodiimide.

The reaction can be carried out in an excess of the condensing agent itself, or the mixture may be diluted with a suitable diluent.

Suitable diluents are all inert organic solvents. These include, in particular, aliphatic and aromatic, optionally halogenated, hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, ethers, such as diethyl and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl and ethyl acetate, nitriles, such as, for example, acetonitrile and propionitrile, benzonitrile and glutarodinitrile, tetramethylene sulphone and hexamethylphosphoric acid triamide. Moreover, lower aliphatic carboxylic acids, such as acetic acid, propionic acid or butyric acid and trifluoroacetic acid.

Catalysts for the cyclization are not absolutely essential. In many cases, however, acceleration of the reaction is achieved by adding a strong acid.

Examples of suitable acids are HCl, $H_2SO_4$, trifluoroacetic acid and toluenesulphonic acid.

The cyclization can be carried out in a temperature range from $-20°$ to $+150°$ C., preferably in the temperature range of $0°-100°$ C.

The process is usually carried out under atmospheric pressure, but it may be advantageous to carry it out under pressure, for example when low-boiling solvents are used.

In carrying out the process according to the invention, at least 1 mol of condensing agent is employed per mol of ureidothiophenecarboxylic acid. Where diluents are employed, a molar ratio of 1–3:1, in particular 1–1.5:1, is preferred. If the condensing agent is at the same time the reaction medium, 3–30 mols, in particular 3–5 mols of condensing agent should be used per mol of ureidothiophenecarboxylic acid.

The reaction products are isolated by filtering off directly precipitated product from the corresponding solvents, or by distilling off the solvent.

If, in process 2(b), 3-amino-4-carboxy-5-methylthiophene and phenyl isocyanide dichloride are used as starting compounds, the course of the reaction can be represented as follows:

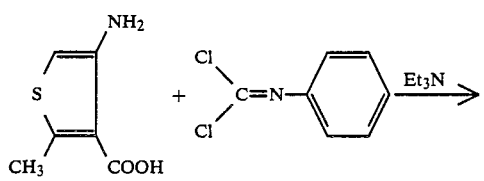

III            IV

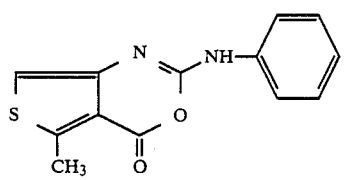

The aminothiophenes of the formula III are known or can be prepared analogously to known processes (K. Gewald et al., Chem. Ber. 98 (1965) page 3571; Chem. Ber. 99 (1966) page 94; EP-OS (European Published Specification) No. 4,931).

Preferred aminothiophenes of the formula III are those in which the radicals $R^5$ and $R^6$ have the preferred meanings stated in the case of compounds of the formula I.

The following may be mentioned individually:

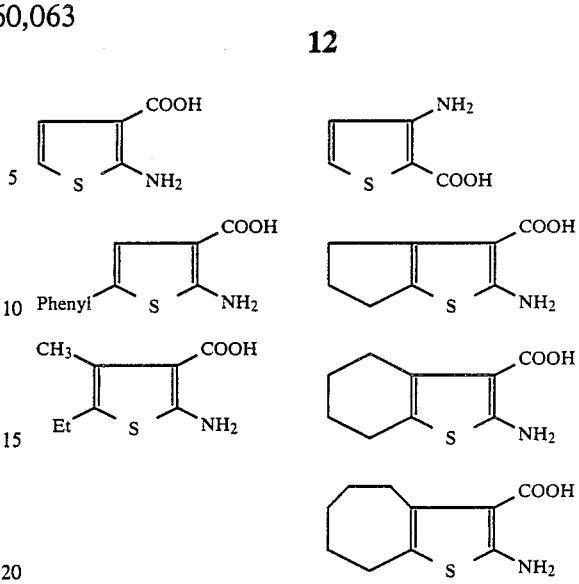

Compounds of the formula IV are known or can be prepared analogously to known processes. Preferred compounds of the formula IV are those in which $R^4$ has the preferred meanings stated in the case of compounds of the formula I.

The following may be mentioned individually: Methyl isocyanide dichloride, ethyl isocyanide dichloride, propyl isocyanide dichloride, isopropyl isocyanide dichloride, n-butyl isocyanide dichloride, isobutyl isocyanide dichloride, tert.-butyl isocyanide dichloride, cyclohexyl isocyanide dichloride and phenyl isocyanide dichloride.

The reaction, according to the invention, between the aminothiophenes of the formula III and the compounds of the formula IV is preferably carried out in the presence of a diluent. Suitable diluents are all inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, ethers, such as diethyl and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl and ethyl acetate, nitriles, such as, for example acetonitrile and propionitrile, benzonitrile and glutarodinitrile, tetramethylene sulphone and hexamethylphosphoric acid triamide.

The reaction is carried out in the presence of acid acceptors.

All customary acid-binding agents can be used as acid acceptors. These preferably include alkali metal carbonates, hydroxides or alcoholates, such as sodium carbonate, potassium carbonate, sodium hydroxide, potassium hydroxide, sodium methylate, potassium methylate, sodium ethylate and potassium ethylate, and aliphatic, aromatic or heterocyclic amines, for example trimethylamine, triethylamine, tributylamine, dimethylaniline, dimethylbenzylamine, pyridine and 4-dimethylaminopyridine.

To accelerate the course of the reaction, catalysts can be added. Compounds which can be used as catalysts are those which usually serve for effecting phase transfer in reactions in two-phase systems consisting of water and water-immiscible organic solvents (phase-transfer catalyst). Particularly preferred catalysts of this type are tetraalkyl- and trialkylaralkyl-ammonium salts having preferably 1 to 10, in particular 1 to 8, carbon atoms per alkyl group, preferably phenyl as the aryl component of the aralkyl group and preferably 1 to 4, in particular 1 or 2, carbon atoms in the alkyl part of the aralkyl groups. Particularly suitable compounds are the halides, such as chlorides, bromides and iodides, preferably the chlorides and bromides. Tetrabutylammonium bromide, benzyl-triethylammonium chloride and methyltrioctylammonium chloride may be mentioned as examples. In addition, 4-dimethylaminopyridine and 4-pyrrolidino-pyridine.

The reaction temperatures can be varied within a relatively wide temperature range. In general, the reaction is carried out at between 0° C. and 120° C., preferably between 20° C. and 70° C.

The reaction is usually carried out under atmospheric pressure, but it may be advantageous to carry it out in closed vessels under pressure, for example when low-boiling isocyanide dichlorides are used.

In carrying out the process according to the invention, at least 1 mol of the compound of the formula IV is employed per mol of aminothiophene. A molar ratio of compounds of the formula IV to aminothiophene of 1–3:1, in particular 1–1.5:1, is preferred. The acid acceptors are added at least in amounts of 2 mols of acid acceptors per mol of isocyanide dichloride. A molar ratio of acid acceptors to isocyanide dichloride of 2–6:1, in particular 2–3:1, is preferred.

The catalysts are preferably used in amounts of 0.01 to 0.1 mol per mol of aminophene.

The reaction products are isolated by directly filtering off the precipitated products from the corresponding solvents, or by distilling off the solvent.

If, in process 2c, 2-N'-isopropylureido-3-tertiary-butoxycarbonyl-4,5-dimethyl-thiophene and a mixture of trifluoroacetic acid and trifluoroacetic anhydride are used, the course of the reaction can be represented as follows:

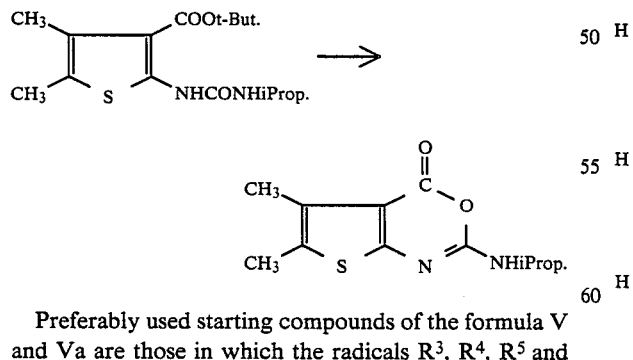

Preferably used starting compounds of the formula V and Va are those in which the radicals $R^3$, $R^4$, $R^5$ and $R^6$ have the preferred meanings mentioned in the case of the compounds of the formula I.

$R^7$ preferably represents t-butyl or benzyl.

The following compounds of the formula V may be mentioned individually:

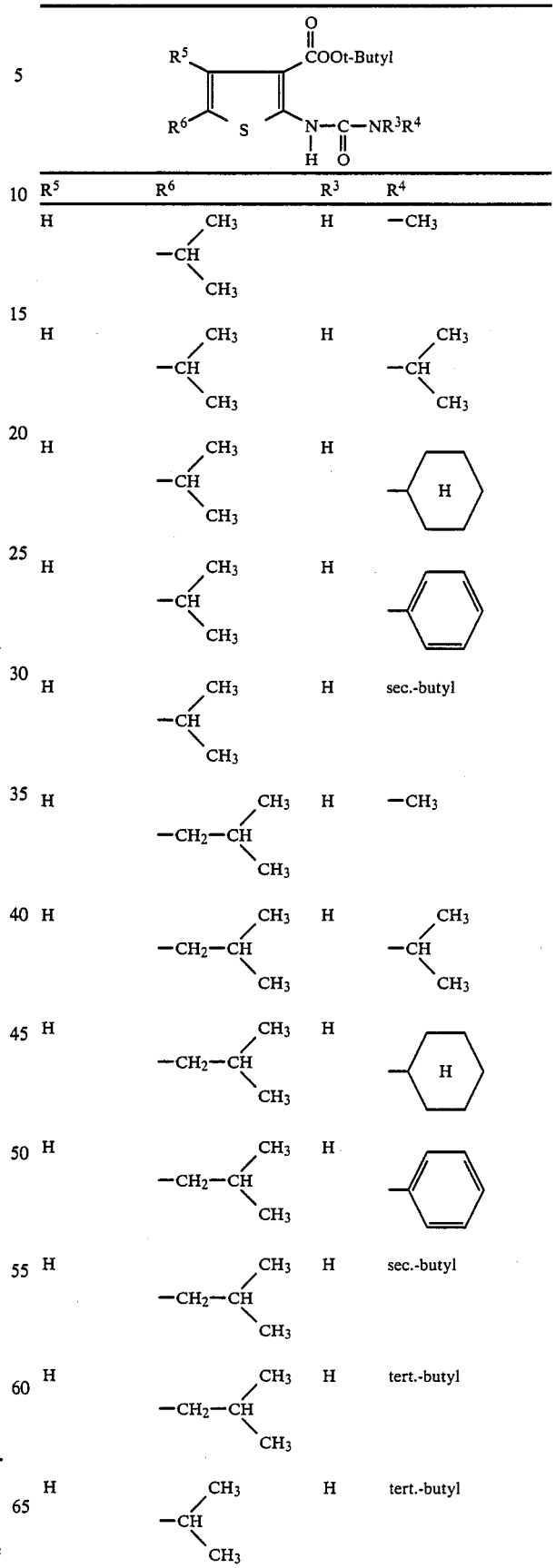

-continued

Structure:
$R^5$, $R^6$ on thiophene ring with $COOt$-Butyl, and $N(H)-C(=O)-NR^3R^4$ substituent.

| $R^5$ | $R^6$ | $R^3$ | $R^4$ |
|---|---|---|---|
| —$CH_3$ | —Et | H | —CH($CH_3$)$_2$ |
| —$CH_3$ | —Et | H | phenyl |
| ($CH_2$)$_3$ | | H | $CH_3$ |
| ($CH_2$)$_3$ | | H | i-propyl |
| ($CH_2$)$_3$ | | H | n-butyl |
| ($CH_2$)$_3$ | | H | cyclohexyl |
| ($CH_2$)$_3$ | | H | phenyl |
| ($CH_2$)$_3$ | | H | 4-chlorophenyl |
| ($CH_2$)$_4$ | | H | $CH_3$ |
| ($CH_2$)$_4$ | | H | i-propyl |
| ($CH_2$)$_4$ | | $CH_3$ | n-butyl |
| ($CH_2$)$_4$ | | $CH_3$ | cyclohexyl |
| ($CH_2$)$_4$ | | $C_2H_5$ | $CH_3$ |
| ($CH_2$)$_4$ | | $CH_3$ | phenyl |
| ($CH_2$)$_4$ | | $CH_3$ | 4-chlorophenyl |
| ($CH_2$)$_4$ | | $C_2H_5$ | i-propyl |
| ($CH_2$)$_4$ | | $CH_3$ | 2-methylphenyl |
| ($CH_2$)$_4$ | | $CH_3$ | 2-methoxyphenyl |
| ($CH_2$)$_4$ | | $C_2H_5$ | n-butyl |
| ($CH_2$)$_5$ | | $CH_3$ | $CH_3$ |
| ($CH_2$)$_5$ | | $CH_3$ | i-propyl |
| ($CH_2$)$_5$ | | $C_2H_5$ | $CH_3$ |
| ($CH_2$)$_5$ | | $CH_3$ | n-butyl |
| ($CH_2$)$_5$ | | $CH_3$ | cyclohexyl |
| ($CH_2$)$_5$ | | $C_2H_5$ | i-propyl |
| ($CH_2$)$_5$ | | $CH_3$ | phenyl |
| ($CH_2$)$_5$ | | $C_2H_5$ | n-butyl |
| ($CH_2$)$_4$ | | H | n-butyl |
| ($CH_2$)$_4$ | | H | cyclohexyl |
| ($CH_2$)$_4$ | | H | phenyl |
| ($CH_2$)$_4$ | | H | 4-methoxyphenyl |
| ($CH_2$)$_5$ | | H | $CH_3$ |
| ($CH_2$)$_5$ | | H | i-propyl |
| ($CH_2$)$_5$ | | H | cyclohexyl |
| ($CH_2$)$_5$ | | H | phenyl |
| ($CH_2$)$_5$ | | H | 4-chlorophenyl |
| H | —$CH_3$ | H | —CH($CH_3$)$_2$ |
| H | —$CH_3$ | H | —$CH_3$ |
| H | —$CH_3$ | H | cyclohexyl (—C$_6$H$_{11}$) |
| H | —$CH_3$ | H | phenyl |
| —CH($CH_3$)$_2$ | H | H | —$CH_3$ |
| —CH($CH_3$)$_2$ | H | H | H |
| —CH($CH_3$)$_2$ | H | H | phenyl |
| —CH($CH_3$)$_2$ | H | H | —CH($CH_3$)$_2$ |
| H | —Et | H | —$CH_3$ |
| H | —Et | H | —CH($CH_3$)$_2$ |
| H | —Et | H | phenyl |
| H | —Et | H | tert.-butyl |
| H | —Et | H | —$CH_3$ |
| —Et | —$CH_3$ | H | —$CH_3$ |
| $CH_3$ | H | H | $CH_3$ |
| $CH_3$ | H | H | i-propyl |
| $CH_3$ | H | H | i-butyl |
| $CH_3$ | H | H | cyclopentyl |
| $CH_3$ | H | H | cyclohexyl |
| $CH_3$ | H | H | phenyl |
| $CH_3$ | H | H | 4-methoxyphenyl |
| H | n-$C_5H_{11}$ | H | $CH_3$ |
| H | n-$C_5H_{11}$ | H | 1-propyl |
| H | n-$C_5H_{11}$ | H | 1-butyl |
| H | n-$C_5H_{11}$ | H | cyclopentyl |
| H | n-$C_5H_{11}$ | H | cyclohexyl |
| H | n-$C_5H_{11}$ | H | phenyl |
| H | n-$C_5H_{11}$ | H | 4-chlorophenyl |
| H | n-$C_5H_{11}$ | H | 4-methoxyphenyl |
| H | Phenyl | H | cyclopropyl |

Some of the compounds of the formula V and Va are known, and some of them form the subject of commonly assigned application Ser. No. 863,647, filed 5/15/86, corresponding to German Pat. No. 3 517 706.3. They are obtained, for example, by reacting appropriately substituted thienylamines with isocyanates or with phosgene and amines in a manner known per se, or by reacting appropriately substituted thienyl isocyanates with amines. The compounds of the formula V and Va can also be prepared analogously to the methods described in DE-OS (German Published Specifications) Nos. 2,122,636 and 2,627,935.

The reaction is carried out in the presence of acidic condensing agents in combination with a dehydrating agent. Examples of acidic condensing agents are concentrated inorganic acids, such as, for example, hydrochloric acid, sulphuric acid, phosphoric acid and polyphosphoric acid, and strong organic acids, such as, for example, trifluoroacetic acid.

Examples of dehydrating agents are trifluoroacetic anhydride, acetic anhydride and carbodiimides, such as, for example, dicyclohexylcarbodiimide.

The reaction is carried out in the presence of diluents. Suitable diluents are all inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, ethers, such as diethyl and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl and ethyl acetate, nitriles, such as, for example, acetonitrile and propionitrile, benzonitrile and glutarodinitrile, and tetramethylene sulphone and hexamethylphosphoric triamide.

The reaction is carried out at temperatures of $-70°$ C. to $+100°$ C., preferably at $-10°$ C. to $+60°$ C..

The reaction is carried out under atmospheric pressure.

In general, 1 mol of condensing agent is employed per mol of the compound of the formula V or Va. Trifluoroacetic anhydride and acetic anhydride are preferred.

The reaction is preferably carried out in a mixture of trifluoroacetic acid and trifluoroacetic anhydride in a ratio of 1:1.

Working up after the end of the reaction is carried out by pouring the mixture into water and filtering off the product, possibly after neutralization has been carried out.

If, in process 4a, 5-bromo-3-tert.-butoxycarbonyl-2-(N'-isobutyl-ureido)-thiophene and trifluoroacetic acid are used as the starting substance, the course of the reaction (for the preparation of the compounds of the formulae II or IIa) can be represented as follows:

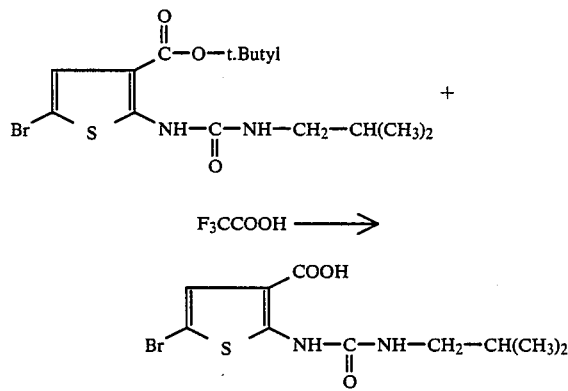

The tert.-butoxycarbonyl-ureidothiophenes are known or can be prepared analogously to known processes (see Le A No. 23 725, application Ser. No. 863,647, supra).

Preferably used starting compounds are ureidothiophenes of the formula V or Va in which the radicals $R^3$, $R^4$, $R^5$ and $R^6$ have the preferred meanings mentioned in the case of the compounds of the formula I, and the radical $R^7$ represents tert.-butyl or benzyl.

The compounds of the formula V which were stated further above may be mentioned individually.

Elimination of the ester radicals is effected, in particular, using strong acids, such as, for example, hydrochloric acid, hydrogen bromide, sulphuric acid, toluenesulphonic acid, methanesulphonic acid or trifluoroacetic acid, and mixtures of these with lower aliphatic carboxylic acids, such as, for example, formic acid, acetic acid or propionic acid.

The reaction can be carried out in the acid used, as a reaction medium, or in the presence of diluents.

Suitable diluents are all inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, ethers, such as diethyl and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, and esters, such as methyl and ethyl acetate.

The reaction temperature is kept between about 0° C. and 130° C., preferably between about 20° C. and 60° C. The process is preferably carried out under atmospheric pressure, but it may be advantageous to carry it out under pressure, for example when volatile acids are used.

The products are isolated by filtering off the precipitated product from the corresponding solvents, or by distilling off the solvent.

If, in process 4b, 5-methyl-thieno[2,3-d]oxazinedione and isobutylamine are used, the reaction may be represented by the following equation:

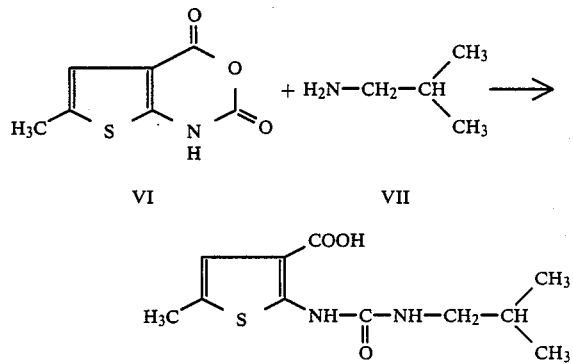

Thienooxazinediones of the formula VI are known or can be prepared by known processes (see G. M. Coppola et al., J. Heterocycl. Chem. 19, 717 (1982), BE No. 852,328).

Preferred thienooxazinediones are those in which the radicals $R^5$ and $R^6$ have the preferred meanings mentioned in the case of the compounds of the formula I and $R^8$ represents hydrogen.

The following compounds of the formula VI may be mentioned individually:

| $R^5$ | $R^6$ |
|---|---|
| H | $-CH(CH_3)_2$ |
| H | $-CH_3$ |
| H | $-CH_2-CH(CH_3)_2$ |

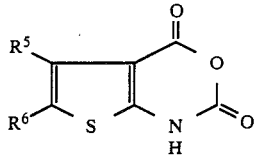

| $R^5$ | $R^6$ |
|---|---|
| —CH₃ | —CH₃ |
| —CH₃ | —C₂H₅ |
| —CH₃ | H |
| H | ⌬ (phenyl) |
| H | —C₂H₅ |
| —(CH₂)₃— | |
| —(CH₂)₄— | |
| —(CH₂)₅— | |

Compounds of the formula VII are known or can be prepared by known processes. Preferred compounds of the formula VII are those in which $R^3$ and $R^4$ have the preferred meanings mentioned in the case of the compounds of the formula I.

The following may be mentioned as examples: methylamine, dimethylamine, ethylamine, diethylamine, n-propylamine, di-n-propylamine, isopropylamine, di-isopropylamine, n-butylamine, i-butylamine, sec.-butylamine, t.-butylamine, cyclopentylamine, cyclohexylamine, aniline, 2-chloroaniline, 3-chloroaniline, 4-chloroaniline, 2-nitroaniline, 3-nitroaniline, 4-nitroaniline, 2-methylaniline, 3-methylaniline, 4-methylaniline, 2-methoxyaniline, 3-methoxyaniline, 4-methoxyaniline, 2-trifluoromethylaniline, 3-trifluoromethylaniline and 4-trifluoromethylaniline.

To prepare the thienylureas of the formula II and IIa, the thienooxazinediones of the formula VI are reacted with at least equimolar amounts of the amine of the formula VII. The reaction can be carried out with or without diluents. When it is carried out without diluents, the amine is preferably employed in an amount of 3–30 mols per mol of thienooxazinedione, particularly preferably 3–10 mols. When the reaction is carried out in the presence of diluents, preferably 1–3 mols, particularly preferably 1–2 mols, of amine are used per mol of thienooxazinedione.

The following may be mentioned as diluents: all inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachlroide, chlorobenzene and o-dichlorobenzene, ethers, such as diethyl and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl and ethyl acetate, nitriles, such as, for example, acetonitrile and propionitrile, benzonitrile and gluatrodinitrile, amides, such as, for example, dimethylformamide, dimethylacetamide and N-methylpyrrolidone, and dimethyl sulphoxide, tetramethylene sulphone and hexamethylphosphoric acid triamide.

To accelerate the course of the reaction, catalysts can be added. Suitable catalysts are: for example, tertiary amines, such as pyridine, 4-dimethylaminopyridine, triethylamine, triethylenediamine or trimethylenetetrahydropyrimidine; tin(II) and tin(IV) compounds, such as tin(II) octoate or tin(IV) chloride. The tertiary amines mentioned as reaction accelerators, for example pyridine, can also be used as solvents.

The reaction temperatures can be varied within a relatively wide temperature range. In general, the reaction is carried out at between 0° C. and 120° C., preferably between 20° C. and 70° C.

The reaction is usually carried out under atmospheric pressure, but it may be advantageous to carry it out in closed vessels under pressure, for example when low-boiling amines are used.

The catalysts are preferably used in amounts of 0.01 to 0.1 mol per mol of the reaction components, but larger amounts, for example of the tertiary amines, may also be used.

The reaction products are isolated by directly filtering off the precipitated products from the corresponding solvents, or by distilling off the solvent.

The active compounds are used as yield promoters for animals in order to promote and accelerate growth, milk production and wool production, and to improve feed utilization and meat quality and to shift the meat/fat ratio in favor of meat. The active compounds are used for livestock, breeding animals, ornamental animals and animals for leisure-time activities.

The livestock and breeding animals include mammals, such as, for example, cattle, pigs, horses, sheep, goats, rabbits, hares and fallow deer, fur-bearing animals, such as mink and chinchilla, poultry, such as, for example, hens, turkeys, geese, ducks and pigeons, fish, such as, for example, carp, trout, salmon, eels, tench and pike, and reptiles, such as, for example, snakes and crocodiles.

The ornamental animals and animals for leisure-time activities include mammals, such as dogs and cats, birds, such as parrots and canaries, and fish, such as ornamental fish and aquarium fish, for example goldfish.

The active compounds are employed during all growth and production phases of the animals, regardless of the sex of the animals. The active compounds are preferably employed during the intensive growth and production phase. The intensive growth and production phase lasts for from one month to 10 years, depending on the animal species.

The amount of the active ingredients which are administered to the animals in order to achieve the desired effect can be varied substantially, owing to the advantageous properties of the active compounds. It is preferably about 0.001 to 50 mg/kg, in particular 0.01 to 5 mg/kg, of body weight per day. The suitable amount of active compound and the suitable duration of administration depend in particular on the species, the age, the sex, the state of health and the method of keeping and feeding the animals, and can be readily determined by any skilled worker.

The active compounds are administered to the animals by the customary methods. The method of administration depends in particular on the species, the behavior and the state of health of the animals.

The active compound can be administered in a single dose. The active compounds can, however, also be administered temporarily or continuously during the entire growth phase or during a part of the growth phase. In the case of continuous administration, the administration can be effected once or several times daily, at regular or irregular intervals.

Administration is effected orally or parenterally in formulations suitable for this purpose or in the pure form. Oral formulations are powders, tablets, granules, doenchs, boluses and feeds, premixes for feeds, and formulations for administration via drinking water.

The oral formulations contain the active compound in concentrations of 0.01 ppm—100%, preferably 0.01 ppm—1%.

Parenteral formulations are injections in the form of solutions, emulsions and suspensions, and implants.

The active compounds can be present in the formulations alone or as a mixture with other active compounds, mineral salts, trace elements, vitamins, proteins, colorants, fats or flavorings.

The concentration of the active compounds in the feed is usually about 0.01–500 ppm, preferably 0.1–50 ppm.

The active compounds can be added to the feed, as such or in the form of premixes or feed concentrates.

Example of the composition of a feed for rearing chicks, which contains the active compound according to the invention:

200 g of wheat, 340 g of corn, 361 g of coarse soy bean meal, 60 g of beef tallow, 15 g of dicalcium phosphate, 10 g of calcium carbonate, 4 g of iodinated sodium chloride, 7.5 g of a vitamin/mineral mixture and 2.5 g of an active compound premix give, after careful mixing, 1 kg of feed.

1 kg of feed mixture contains:

600 I.U. of Vitamin A, 100 I.U. of Vitamin, $D_3$, 10 mg of Vitamin E, 1 mg of Vitamin $K_3$, 3 mg of riboflavin, 2 mg of pyridoxin, 20 mcg of Vitamin $B_{12}$, 5 mg of calcium pantothenate, 30 mg of nicotinic acid, 200 mg of choline chloride, 200 mg of $MnSO_2 \times H_2O$, 140 mg of $ZnSO_4 \times 7H_2O$, 100 mg of $FeSO_4 \times 7H_2O$ and 20 mg of $CuSO_4 \times 5H_2O$.

2.5 g of active compound premix contain, for example, 10 mg of active compound and 1 g of DL-methionine, the remainder being soy bean flour.

Example of the composition of a feed for rearing pigs, which contains the active compounds according to the invention:

630 g of shredded cereal feed (composed of 200 g of corn 150 g of shredded barley, 150 g of shredded oats and 130 g of shredded wheat, 80 g of fish meal, 60 g of coarse, soy bean meal, 60 g of tapioca meal, 38 g of brewer's yeast, 50 g of a vitamin/mineral mixture for pigs, 30 g of linseed cake meal, 30 g of corn gluten feed, 10 g of soy bean oil, 10 g of sugar cane molasses and 2 g of an active compound premix (composition, for example, as for chickfeed) gives, after careful mixing, 1 kg of feed.

The feed mixtures indicated are intended preferably for rearing and fattening chicks or pigs, respectively, but they can also be used, in the same or a similar composition, for feeding other animals.

EXAMPLE A

Rat feeding test

Female laboratory rats of the SPF Wistar type (Hagemann breed) weighing 90–110 g are fed ad lib with standard rat feed to which the desired amount of active compound has been added. Each test is carried out using feed from the same batch, so that differences in the composition of the feed cannot impair the comparability of the results.

The rats receive water ad lib.

12 rats form each test group and are fed with feed to which the desired amount of active compound has been added. A control group receives feed without active compound. The mean body weight and the scatter in the body weights of the rats is the same in each test group, so that a comparability of the test groups between one another is ensured.

During the 13-day test, weight increase and feed consumption are determined.

The results shown in the table are obtained:

TABLE

| Rat feeding test | |
|---|---|
| Active compound Dose 25 ppm | Weight increase |
| Control, without active compound | 100 |
| 16 | 104 |
| 19 | 104 |
| 21 | 102 |
| 4 | 119 |
| 5 | 113 |

Preparation of the compounds of the formula I according to process 2c:

EXAMPLE 1(c)

11 g (32 mmol) of 4,5-dimethyl-3-tert.-butoxycarbonyl-2-N′-phenylureidothiophene were introduced into a mixture of 7.34 g (35 mmol) of trifluoroacetic anhydride and 32 ml of trifluoroacetic acid at room temperature, while stirring, and stirring was then continued for a further hour. The mixture was worked up by adding it dropwise to 500 ml of saturated $NaHCO_3$ solution, with thorough stirring, and the precipitate was filtered off under suction.

The product was purified by recrystallization from toluene.

Yield: 5.2 g (60% of theory).

Melting point 227° C. (immediately becomes solid again).

The following examples were obtained analogously:

| Example No. | $R^5$ | $R^6$ | $R^4$ | Melting point °C. |
|---|---|---|---|---|
| 2 | $CH_3$ | $CH_3$ | $CH_3$ | 198 (decomposition) |
| 3 | $CH_3$ | $CH_3$ | i-$C_3H_7$ | 200 (decomposition) |
| 4 | $CH_3$ | $CH_3$ | i-$C_4H_9$ | 172 |
| 5 | H | H | —$CH_3$ | 196 (decomposition) |
| 6 | H | H | i-propyl | 172 |
| 7 | H | H | i-butyl | 162 |
| 8 | H | H |  | 185 |
| 9 | H | H | t-butyl | 168 |
| 10 | H | $CH_3$ | —$CH_3$ | 210 (decomposition) |
| 11 | H | $CH_3$ | i-propyl | 190 |
| 12(c) | H | $CH_3$ | i-butyl | 172 |

| Example No. | $R^4$ | $R^5$—$R^6$ | melting point (°C.) |
|---|---|---|---|
| 13 | $CH_3$ | $(CH_2)_4$ | 195 |
| 14 | i-$C_3H_7$ | $(CH_2)_3$ | 206 |
| 15 | t-$C_4H_9$ | $(CH_2)_3$ | 167 |
| 16 | 2-$CH_3O$—$C_6H_4$ | $(CH_2)_3$ | 206 |
| 17 | t-$C_4H_9$ | $(CH_2)_4$ | 209 |
| 18 | 2-$CH_3O$—$C_6H_4$ | $(CH_2)_4$ | 182–3 |
| 19 | i-$C_3H_7$ | $(CH_2)_5$ | 226 |
| 20 | t-$C_4H_9$ | $(CH_2)_5$ | 191 |

| 21 | i-C$_3$H$_7$ | (CH$_2$)$_4$ | 203 |
| 22 | n-C$_4$H$_9$ | (CH$_2$)$_3$ | 185 |

Preparation of the compounds of the formula I according to process 2b:

EXAMPLE 1(b)

1.15 g (6.7 mmol) of 4,5-dimethyl-2-aminothiophene-3-carboxylic acid were dissolved in 20 ml of dry chloroform, and 1.7 g (16.9 mmol) of triethylamine and 1.27 g (7.3 mmol) of phenyl isocyanide dichloride were added. Thereafter, the mixture was boiled under reflux for 8 hours. To work up the mixture, 100 ml of water were added, and the organic phase was separated off and washed with three times 100 ml of 5% strength NaH$_2$PO$_4$ solution. The solvent was distilled off in vacuo, and the residue was chromatographed over silica gel, using dichloromethane as the mobile phase.

Yield: 190 mg (10.4% of theory).

Melting point: 226°–7° C. (immediately becomes solid again).

Preparation of the compounds of the formula I according to process 2a:

EXAMPLE 12(a)

A suspension of 588 mg (2.3 mmol) of 3-carboxy-5-methyl-2-(N'-isobutylureido)-thiophene and 0.26 g (2.5 mmol) of acetic anhydride in 5 ml of dry toluene was heated to 60° C. for 8 hours, while stirring. To work up the mixture, 50 ml of CHCl$_3$ were added, and the mixture was washed twice with NaHCO$_3$ solution and evaporated down until crystallization began. 50 ml of petroleum ether were added, the mixture was allowed to stand for 15 minutes, and the product was filtered off under suction.

Yield: 300 mg (54.8% of theory).

Melting point: 173° C.

Preparation of the starting materials

EXAMPLE (a)

Preparation of the compounds of the formula II according to process 4a 800 mg (2.56 mmol) 3-t-butoxycarbonyl-2-(N'-isobutylureido)-5-methyl-thiophene were added to a mixture of 2 ml of trifluoroacetic acid and 5 ml of dichloromethane, and the mixture was stirred overnight. It was then evaporated down in vacuo, in the final stage under reduced pressure from an oil pump.

Yield: 643 mg (98% of theory).

Melting point: 188°–9° C. (decomposition).

EXAMPLE (b)

Preparation of the compounds of the formula II according to process 4b 5 g (27.3 mmol) of 5-methylthieno[2,3-d]-3-H-oxazine-2,7-dione and 3.5 g (59 mmol) of isopropylamine are dissolved in 30 ml of dry DMF, and the solution is stirred for 2 hours at room temperature. The mixture is worked up by pouring it into 200 ml of water, acidifying it with dilute HCl and extracting it with CHCl$_3$. The solvent is distilled off in vacuo, and the residue is recrystallized from toluene.

Yield: 1.39 g (21% of theory).

Melting point: 181° C. (decomposition).

Preparation of the compounds of the formula V

EXAMPLE c(1)

4,5-Dimethyl-3-tert.-butoxycarbonyl-2-N'-isobutylureidothiophene 14.3 g (0.144 mol) of isobutyl isocyanate were added to 16 g (70.5 mmol) of 4,5-dimethyl-3-tert.-butoxycarbonyl-2-aminothiophene, and the mixture was stirred for 18 hours at 50° C. After the mixture had been cooled, it was stirred into 1 l of 2.5N aqueous hydrochloric acid, and the solid urea precipitated was filtered off under suction.

Purification was carried out by recrystallization from ethanol.

Yield: 6.9 g (30% of theory).

Melting point: 173° C.

EXAMPLE c(2)

4,5-Dimethyl-3-tert.-butoxycarbonyl-2-N'-phenylureidothiophene 24 ml (46 mmol) of a 1.93M phosgene solution in toluene were added dropwise to a solution of 10 g (44 mmol) of 4,5-dimethyl-3-tert.-butoxycarbonyl-2-aminothiophene and 9.8 g (97 mmol) of triethylamine in 200 ml of dry chloroform at $-10°$ C. When the addition was complete, stirring was continued for a further 15 minutes without cooling, after which 4.5 g (48 mmol) of aniline were added dropwise, and stirring was continued for a further hour at room temperature. The mixture was worked up by pouring it onto 1 l of water, and separating off the organic phase and washing it with twice 200 ml of 5% strength aqueous NaH$_2$PO$_4$ solution. After the mixture had been dried with Na$_2$SO$_4$, the solvent was distilled off in vacuo, and the residue was recrystallized from toluene.

Yield: 11.8 g (77% of theory).

Melting point: 218° C.

The following compounds were obtained analogously to one of these processes:

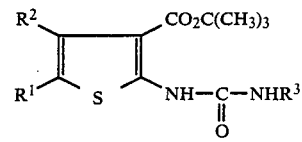

| Example No. | R$^1$ | R$^2$ | R$^3$ | Mp. |
| --- | --- | --- | --- | --- |
| c3 | CH$_3$ | CH$_3$ | CH$_3$ | 149 |
| c4 | CH$_3$ | CH$_3$ | i-C$_3$H$_7$ | 186 |
| c5 | H | H | CH$_3$ | 160 |
| c6 | H | H | i-C$_3$H$_7$ | 207 |
| c7 | (CH$_2$)$_3$ | | i-C$_3$H$_7$ | 182 |
| c8 | (CH$_2$)$_4$ | | CH$_3$ | 150 |
| c9 | (CH$_2$)$_4$ | | i-C$_3$H$_7$ | 182 |
| c10 | (CH$_2$)$_5$ | | i-C$_3$H$_7$ | 193 |

It is understood that the specification and examples are illustrative but not limitative of the present invention and that other embodiments within the spirit and scope of the invention will suggest themselves to those skilled in the art.

What is claimed is:

1. A thienoxazinone of the formula

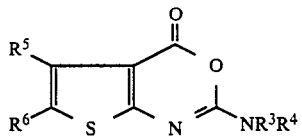

I.

or

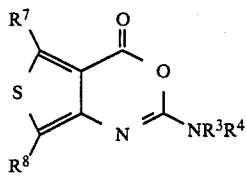

II.

in which

R$^5$, R$^6$, R$^7$ and R$^8$ each indpendently represents hydrogen, halogen, nitro, CN, C$_{1-4}$-alkoxy, C$_{1-4}$-alkylthio, optionally substituted by C$_{1-6}$-acyl, or optionally substituted aroyl, or C$_{1-6}$-alkyl which is optionally substituted by halogen, C$_{1-4}$-alkoxy, C$_{1-4}$-alkylthio, aryl, aryloxy, arylthio, amino, C$_{1-4}$-alkylamino, di-C$_{1-4}$-alkylamino or arylamino, or represents phenyl, the phenyl radicals optionally carrying one or more substituents selected from the group consisting of halogen, C$_{1-4}$-alkyl, CN, C$_{1-4}$-alkoxy, C$_{1-4}$-alkylthio, phenyl, phenoxy, phenylthio, amino, C$_{1-4}$-alkylamino, di-C$_{1-4}$-alkylamino, C$_{1-4}$-alkoxyalkyl, C$_{1-4}$-halogenoalkyl, C$_{1-4}$-halogenoalkoxy, C$_{1-4}$-halogenoalkylthio, methylenedioxy or ethylenedioxy, which are optionally halogen-substituted, or acyl, or R$^5$ and R$^6$, together with the two adjacent C atoms represent a carbocyclic radical having 5–8 ring members which is optionally substituted by OH, C$_{1-4}$-alkyl, halogen, nitro, CN, C$_{1-4}$-alkoxy, C$_{1-4}$-alkylthio, phenyl, phenoxy, phenylthio, amino, C$_{1-4}$-alkylamino, C$_{1-4}$-dialkylamino, C$_{1-4}$-halogenoalkyl, C$_{1-4}$-halogenoalkoxy, C$_{1-4}$-halogenoalkylthio or C$_{1-4}$-alkoxyalkyl, R$^3$ represents hydrogen, and R$^4$ represents C$_{1-4}$-alkyl which is optionally substituted by halogen, C$_{1-4}$-alkoxy, C$_{1-4}$-alkylthio, aryl, aryloxy, arylthio, or amino, or represents phenyl, the phenyl radicals optionally carrying one or more substituents selected from the group consisting of halogen, C$_{1-4}$-alkyl, CN, C$_{1-4}$-alkoxy, C$_{1-4}$-alkylthio, phenyl, phenoxy, phenylthio, amino, C$_{1-4}$-alkylamino, di-C$_{1-4}$-alkylamino C$_{1-4}$-halogenoalkoxy, C$_{1-4}$-halogenoalkylthio, methylenedioxy or ethylenedioxy, which are optionally halogen-substituted, or acyl.

2. A compound according to claim 1, in which

R$^1$ and R$^2$ represents a thiophene ring which is fused to the oxazinone ring in the 2,3-position and is substituted by the radicals R$^5$ and R$^6$, R$^5$ and R$^6$ each independently represents hydrogen or C$_{1-6}$-alkyl which is optionally substituted by fluorine, chlorine or bromine, or represents phenyl which is optionally substituted by C$_{1-4}$-alkyl, halogen, C$_{1-4}$-halogenoalkyl, in particular trifluoromethyl, or C$_{1-4}$-halogenoalkoxy, or represents nitro or acyl, or R$^5$ and R$^6$, together with the adjacent C atoms, represent a saturated 5- to 8-membered carbocyclic ring which is optionally substituted by C$_{1-4}$-alkyl, or together with the adjacent C atoms represent a fused benzene ring which is optionally substituted by halogen, nitro or C$_{1-4}$-alkyl, R$^3$ represents hydrogen, and R$^4$ represents C$_{1-6}$-alkyl or cycloalkyl having up to 8 C atoms or represents phenyl which is optionally substituted by halogen.

3. A compound according to claim 1, in which

R$^1$ and R$^2$, together with the adjacent C atoms, represent a thiophene ring which is fused in its 2,3-positions to the oxazinone ring and is substituted by R$^5$ and R$^6$, R$^5$ and R$^6$ each independently represents hydrogen, C$_{1-4}$-alkyl, acetyl, phenyl or nitro, or R$^5$ and R$^6$ together represent a cyclopentane, cyclohexane, cycloheptane, cyclooctane, cyclohexanone or benzene ring which is fused to the thiophene ring and optionally can be substituted by C$_{1-4}$-alkyl, halogen or nitro, R$^3$ represents hydrogen, and R$^4$ represents C$_{1-6}$-alkyl, cycloalkyl having up to 6 C atoms, or phenyl which is optionally substituted by halogen.

4. A non-human growth animal promoting composition comprising a diluent and an animal growth promoting effective amount of a compound according to claim 1.

5. A composition according to claim 5, wherein the diluent is an edible feed base.

6. A method of promoting the growth of a non-human animal which comprises administering to such animal a growth promoting effective amount of a compound according to claim 1.

* * * * *

UNITED STATES PATENT AND TRADEMARK OFFICE
CERTIFICATE OF CORRECTION

PATENT NO. : 4,760,063
DATED : July 26, 1988
INVENTOR(S) : Werner Hallenback, et al It is certified that error appears in the above-identified patent and that said Letters Patent is hereby corrected as shown below:

| | |
|---|---|
| Col. 26, lines 4-6 | Delete "$R^1$....radicals $R^5$ and $R^6$," |
| Col. 26, line 7 | Delete "$R^5$ and $R^6$" and substitute --$R^5$, $R^6$, $R^7$ and $R^8$-- |
| Col. 26, line 15 | Delete "saturated" |
| Col. 26, line 25 | After "compound" insert --of formula I-- |
| Col. 26, lines 26-29 | Delete "$R^1$....substituted b y $R^5$ and $R^6$" |
| Col. 26, lines 32-34 | Delete "cyclopentane, cyclohexane...to the thiophene ring" and substitute --propylene, butylene, pentylene, hexylene or butadienylene group-- |
| Col. 26, line 41 | Delete "A non-human growth animal" and substitute --A non-human animal growth-- |
| Col. 26, line 45 | Delete "claim 5" and substitute --claim 4-- |

Signed and Sealed this

Twenty-eighth Day of February, 1989

Attest:

DONALD J. QUIGG

Attesting Officer

Commissioner of Patents and Trademarks